US 6,590,737 B2

(12) United States Patent
Imamura

(10) Patent No.: US 6,590,737 B2
(45) Date of Patent: Jul. 8, 2003

(54) METHOD OF MEASURING THE COEFFICIENT OF FRICTION BETWEEN A HEAD SLIDER AND MAGNETIC MEDIUM BY TAKING INTO ACCOUNT THE ADSORPTIVE COMPONENT OF FRICTION

(75) Inventor: Takahiro Imamura, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 69 days.

(21) Appl. No.: 09/790,098

(22) Filed: Feb. 21, 2001

(65) Prior Publication Data

US 2001/0008476 A1 Jul. 19, 2001

Related U.S. Application Data

(63) Continuation of application No. PCT/JP99/00411, filed on Jan. 2, 1999.

(30) Foreign Application Priority Data

Aug. 21, 1998 (JP) ............................................. 10-235544

(51) Int. Cl.$^7$ ........................... G11B 5/012; G01N 19/02
(52) U.S. Cl. ........................................ 360/97.01; 73/9
(58) Field of Search .................... 73/7, 9; 360/97.01, 360/97.02, 237.1, 234

(56) References Cited

U.S. PATENT DOCUMENTS 5,859,357 A * 1/1999 Kameyama ...................... 73/9

FOREIGN PATENT DOCUMENTS

| JP | 11-95301 | 8/1989 |
| JP | 1-221639 | * 9/1989 |
| JP | 2-45733 | 2/1990 |
| JP | 2-198337 | 8/1990 |
| JP | 7-65528 | 3/1995 |
| JP | 9-81924 | 3/1997 |
| JP | 9-089693 | 4/1997 |
| JP | 9-2811020 | 10/1997 |

* cited by examiner

Primary Examiner—A. J. Heinz
(74) Attorney, Agent, or Firm—Greer, Burns & Crain, Ltd.

(57) ABSTRACT

An adsorptive tangential force is measured at the moment when a slider has contacted or touched a receiving surface. The adsorptive tangential force is induced solely by the adsorption transmitted from the receiving surface to the slider. An overall tangential force transmitted from the receiving surface to the slider is measured when the slider is kept urged against the receiving surface. The coefficient of dynamic friction is calculated based on the differential between the thus measured overall and adsorptive tangential forces. The effect of the adsorption can be eliminated from the calculated coefficient of dynamic friction. It is possible to derive the coefficient of dynamic friction at a still higher accuracy.

18 Claims, 5 Drawing Sheets

METHOD OF MEASURING THE COEFFICIENT OF FRICTION BETWEEN A HEAD SLIDER AND MAGNETIC MEDIUM BY TAKING INTO ACCOUNT THE ADSORPTIVE COMPONENT OF FRICTION

This is a continuation based on International Application PCT/JP99/00411, filed Jan. 2, 1999, which application has been published in Japanese, but not in English.

BACKGROUND OF THE INVENTION

1. Field of the Invention

The present invention relates to a method of measuring the coefficient of friction established between a slider or a contacting member and a receiving surface in contact with the slider or the contacting member, and in particular, to a method of measuring the coefficient of friction between a head slider carrying an electromagnetic transducer and the surface of a magnetic disk in a magnetic medium drive or storage device.

2. Description of the Prior Art

A contact head slider is proposed in the technical field of a magnetic medium drive or storage device such as a hard disk drive. The contact head slider designed to keep contacting the surface of a magnetic recording medium is supposed to contribute to realization of a still higher recording density in the magnetic medium drive. It is required to evaluate the friction between the head slider and the surface of the magnetic recording medium at a higher accuracy when the realization of the contact head slider is intended.

For example, Japanese Patent Laid-open No. 2-198337 discloses a conventional method of measuring the coefficient of friction. The method comprises urging a slider against the surface of a magnetic disk under a constant urging force when the magnetic disk rotates at a constant velocity. The friction is then measured between the urged slider and the surface of the rotating magnetic disk. The coefficient of friction is simply derived from calculation based on the detected friction and the magnitude of the urging force.

A lubricating agent or oil usually spreads over the surface of the magnetic disk so as to suppress the abrasion of the head slider and/or the magnetic disk in the magnetic disk drive. The lubricating agent or oil is supposed to establish an adsorption acting on the lightweight slider. The slider is supposed to always suffer from the adsorption irrespective of application of the urging force when the slider contacts the surface of the magnetic disk. The conventional method of measuring inevitably results in derivation of the coefficient of friction larger than the true or actual value because of the effect of the adsorption. This is because the detected friction acting on the slider includes a component induced under the influence of the adsorption. The conventional method of measuring the coefficient of friction fails to take account of the effect of the adsorption.

SUMMARY OF THE INVENTION

It is accordingly an object of the present invention to provide a method of measuring the still accurate coefficient of kinetic friction for a slider or contacting member receiving adsorption from a receiving surface.

According to a first aspect of the present invention, there is provided a method of measuring a coefficient of friction, comprising: moving a receiving surface; applying to a slider a vertical driving force perpendicular to the receiving surface until the slider contacts the receiving surface; measuring an adsorptive tangential force transmitted from the receiving surface to the slider at a moment when the slider contacts the receiving surface; and measuring an overall tangential force transmitted from the receiving surface to the slider when the slider is urged against the receiving surface with an urging force.

The adsorptive tangential force is supposed to represent a separate tangential force generated solely by the adsorption without a component under the influence of the friction generated by the urging force. The measurement of the adsorptive tangential force simply leads to observation or analysis of the independent adsorption. When the measured adsorptive tangential force is taken out of the overall tangential force, it is possible to derive the friction generated solely by the urging force or normal reaction between the receiving surface and the slider without the influence of the adsorption. The thus derived pure friction contributes to derivation or calculation of the still accurate coefficient of friction between the receiving surface and the slider. The influence of the adsorption can totally be eliminated in derivation or calculation of the coefficient of friction. Moreover, the magnitude of the adsorption can additionally be derived.

In estimating the coefficient of friction, the method may include: calculating a differential between the overall and adsorptive tangential forces; and calculating a differential between the vertical driving force keeping the contact of the slider against the receiving surface and an initial contact vertical driving force, for example. The differential between the vertical driving forces is supposed to represent the urging force urging the slider against the receiving surface. Accordingly, if the differential between the tangential forces is divided by the differential between the vertical driving forces, the coefficient of dynamic friction can be derived. Here, the initial contact vertical driving force represents a vertical driving force at the moment when the slider has just contacted or touched the receiving surface. The differential between the overall and adsorptive tangential forces is supposed to correspond to the pure friction without the influence of the adsorption. As a result, the still accurate coefficient of dynamic friction can be derived.

It is preferable to periodically vary the vertical driving force in the aforementioned method of measuring. The method is allowed to repeat step of moving the slider toward the receiving surface until the slider contacts the receiving surface and the step of urging the slider against the receiving surface. Measurement of the adsorptive and overall tangential forces is also repeated. It is possible to eliminate the effect of any disturbance to the utmost so as to derive a still further accurate coefficient of dynamic friction.

The adsorptive and overall tangential forces may be calculated based on a tangential spring constant of a support spring supporting the slider and a displacement of the slider in a direction along the receiving surface, for example, since the product of the tangential spring constant and the displacement of the slider is equivalent to the tangential force. A laser Doppler velocimeter (LDV) can be employed to detect the displacement of the slider, for example.

The method of measuring may be designed to continuously increase the vertical driving force so as to generate the urging force. The variation is measured in the vertical driving force. Also, the variation is measured in the tangential forces from the moment when the adsorptive tangential force has occurred until the overall tangential force reaches a maximum. The comparison between the variations serves to reveal the initial contact vertical driving force established at the moment when the adsorptive tangential force starts to solely act on the slider.

The initial contact vertical driving force can be calculated based on a vertical spring constant of a support spring supporting the slider and a displacement of the slider in a direction toward the receiving surface, for example, since the product of the vertical spring constant and the displacement of the slider is equivalent to the vertical driving force. In this case, an electrostatic actuator can be employed to generate the displacement of the slider, for example. If a predetermined relationship can be determined between the applied voltage and the driving force in the electrostatic actuator, the driving force can be estimated based on the magnitude of the applied voltage. Alternatively, the initial contact vertical driving force may be calculated based on the vertical spring constant of the support spring and the displacement of the slider in the direction vertical to the receiving surface. A laser Doppler velocimeter may be employed to detect the displacement of the slider in the direction vertical to the receiving surface.

According to a second aspect of the present invention, there is provided a method of measuring a coefficient of friction, comprising: moving a receiving surface; urging a slider against the receiving surface with a first load; urging the slider against the receiving surface with a second load larger than the first load; and measuring a tangential force transmitted from the receiving surface to the slider when the first and second loads are respectively applied to the slider.

The adsorption of the receiving surface influences equally to the tangential force induced by the first load and the tangential force induced by the second load. The differential between the tangential forces is supposed to reflect the magnitude of the tangential force induced solely by the friction in response to the normal reaction from the receiving surface. The influence of the adsorption can thus be eliminated. If the coefficient of dynamic friction is derived from the thus estimated friction between the receiving surface and the slider, it is possible to derive or calculate the still accurate coefficient of dynamic friction, independent of the effect of the adsorption between the receiving surface and the slider. In calculating the coefficient of dynamic friction, a predetermined differential is preferably set between the first and second loads, for example. The divide of the differential between the tangential forces by the predetermined differential between the loads leads to derivation of the coefficient of dynamic friction.

In this case, it is preferable to periodically vary the load within a range including the aforementioned first and second loads. The first and second loads may alternately be applied to the slider. Measurement of the tangential force is repeated. It is possible to eliminate the effect of any disturbance to the utmost so as to derive a still further accurate coefficient of dynamic friction.

The tangential force may be calculated based on a tangential spring constant of a support spring supporting the slider and a displacement of the slider in a direction along the receiving surface, for example, since the product of the tangential spring constant and the displacement of the slider is equivalent to the tangential force. A laser Doppler velocimeter (LDV) can be employed to detect the displacement of the slider, for example.

In realizing the aforementioned methods, a specific head slider may be incorporated within a magnetic disk drive. The head slider may include: a slider body having a bottom surface opposed to a magnetic disk; a contacting member supported on the slider body for movement relative to the slider body; and a driving power source disposed on the slider body so as to generate an urging force for urging the contacting member against the magnetic disk.

Employment of the head slider enables measurement for the coefficient of dynamic friction in a condition similar to the actual environment of a general head slider to be incorporated in a magnetic disk drive. For example, employment of an electrostatic actuator as a driving power source enables generation of a tiny or smaller vertical driving force or a load in a facilitated manner. The electrostatic actuator serves to achieve an accurate observation or evaluation for the behavior of the head slider.

A capacitance displacement sensor may be employed to detect the displacement of the contacting member incorporated in the head slider. The capacitance displacement sensor may be mounted on the slider body. When the contacting member is allowed to receive electromagnetic transducers or read/write head elements, it is possible to measure the coefficient of dynamic friction and the adsorption in a condition still similar to the actual environment of a general magnetic disk drive.

The aforementioned methods can be employed to measure the coefficient of friction for any types of the receiving surface including a disk or recording medium in addition to the magnetic recording disk.

BRIEF DESCRIPTION OF THE DRAWINGS

The above and other objects, features and advantages of the present invention will become apparent from the following description of the preferred embodiments in conjunction with the accompanying drawings, wherein.

DESCRIPTION OF THE PREFERRED EMBODIMENTS

Figure 1:
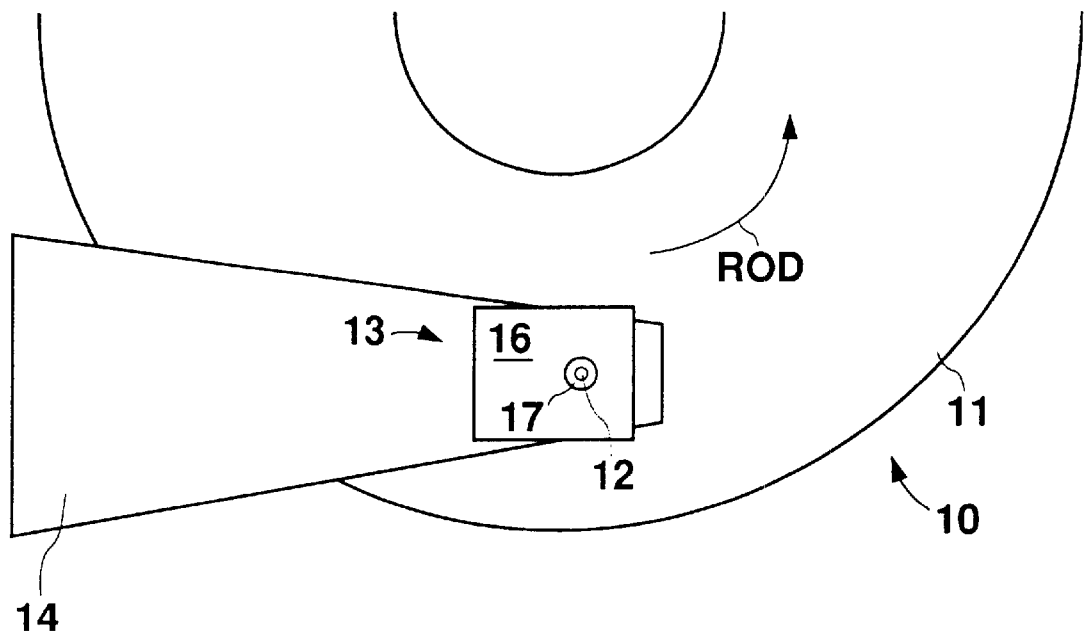
FIG. 1 is a plan view illustrating a part of a measuring apparatus for the coefficient of friction according to the present invention.

FIG. 1 illustrates a plan view of a measuring apparatus for deriving a coefficient of friction according to the present invention. The measuring apparatus 10 includes a magnetic disk 11 rotatable around the rotational axis with the assistance of a spindle motor, not shown, in the same manner as a general magnetic disk drive or storage device. The magnetic disk 11 is made of a transparent material such as a glass, a quartz, and the like.

Figure 2:
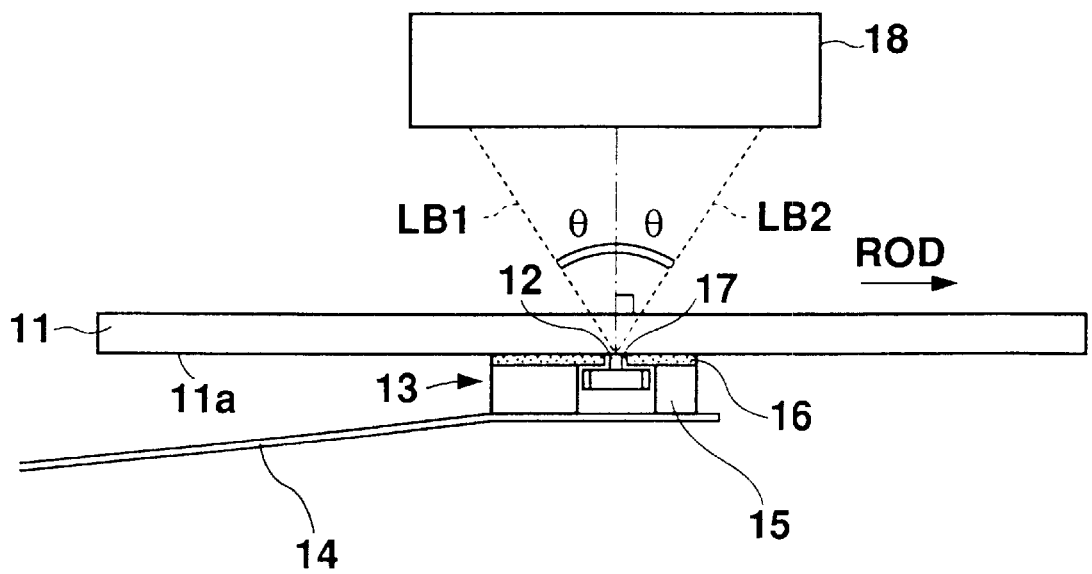
FIG. 2 is a side view along with a partial sectional view illustrating the measuring apparatus.

Referring also to FIG. 2, a head slider 13 is opposed to the backside of the magnetic disk 11, namely, a receiving surface 11a. A contacting member 12 is incorporated in the head slider 13. The head slider 13 is carried at the tip end of an elastic head suspension 14 which extends from the tip end of a carriage, not shown. The carriage may be rotatable around a support shaft in the same manner as a general magnetic disk drive. Alternatively, the head suspension 14 may extend from the tip end of a stationary carriage, not shown.

The head slider 13 includes a slider body 15. An insulating bottom layer 16 is attached to the slider body 15 for defining an air bearing surface opposed to the receiving surface 11a on the magnetic disk 11. The tip end of the contacting member 12 is designed to enter an opening 17 defined in the insulating bottom layer 16. The contacting member 12 opposes its tip end, penetrating through the opening 17, to the receiving surface 11a on the magnetic disk 11.

When the magnetic disk 11 is driven to rotate, the air bearing surface of the insulating bottom layer 16 receives the airflow generated along the receiving surface 11a. A lift is generated to act on the slider body 15 so as to keep the slider body 15 distanced form the receiving surface 11a. The head slider 13 is thus allowed to fly above the receiving surface 11a. The lift is balanced with the resilient force of the head suspension 14 so as to set a predetermined flying height of the head slider 13. The insulating bottom layer 16 may further include a rail or rails, not shown, extending along the surface of the insulating bottom layer 16, protrusions, not shown, standing on the surface of the insulating bottom layer 16 toward the receiving surface 11a, and the like. As conventionally known, such a rail is designed to define the air bearing surface at the top surface. Such a protrusion is designed to reduce the contact area between the air bearing surface and the receiving surface 11a so as to suppress the adsorption transmitted to the head slider 13 from a lubricating agent or oil spreading over the receiving surface 11a.

A laser Doppler velocimeter (LDV) 18 is disposed above the front side of the magnetic disk 11. The laser Doppler velocimeter 18 is designed to irradiate a pair of laser beams LB1, LB2 toward the magnetic disk 11. The incidence angle θ of the laser beams LB1, LB2 is defined between the direction of the laser beam LB1, LB2 and the direction normal to a plane extending in the direction of rotation ROD of the magnetic disk 11. The laser beams LB1, LB2 are allowed to pass through the transparent magnetic disk 11 so as to reach the tip end of the contacting member 12 penetrating through the opening 17. As conventionally known, the laser Doppler velocimeter 18 is designed to detect the speed and the angle of the laser beams LB1, LB2 reflected from the contacting member 12. The velocity of the contacting member 12 is thus derived in the direction of rotation ROD of the magnetic disk 11, namely, the direction of movement of the receiving surface 11a as well as in the direction vertical to the receiving surface 11a, based on the Doppler effect. It is preferable to employ a microscope, not shown, so as to precisely point the laser beams LB1, LB2 at the tip end of the contacting member 12.

Figure 3:
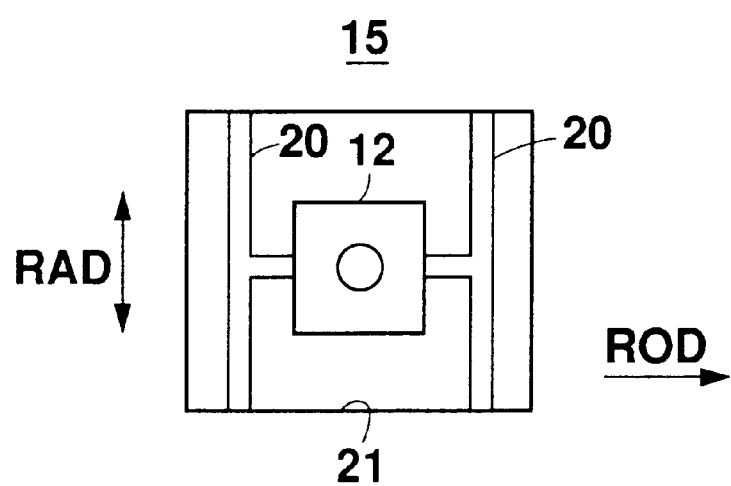
FIG. 3 is a plan view illustrating a support mechanism for supporting a contacting member on a slider body.
Figure 4:
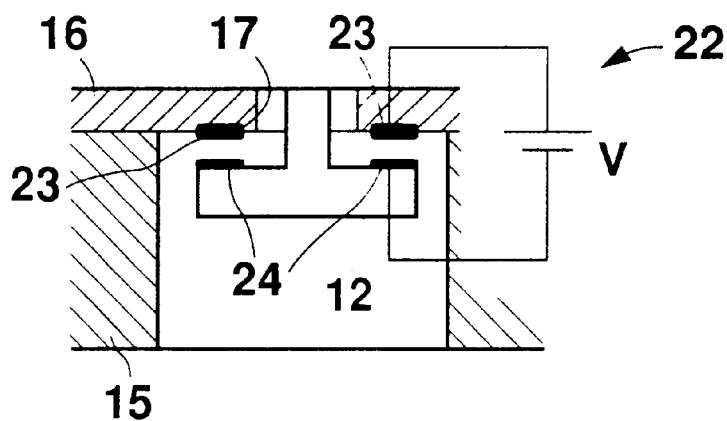
FIG. 4 is a partial sectional view of the slider body for illustrating the structure of an electrostatic actuator.

As shown in FIG. 3, elastic support beams 20 are employed to support the contacting member 12 within a window opening 21 defined in the slider body 15. The elastic support beams 20 are designed to establish a spring constant ky in the direction of rotation ROD so as to accept the displacement of the contacting member 12 relative to the slider body 15 in the direction of rotation ROD of the magnetic disk 11, namely, in the direction along the receiving surface 11a. Simultaneously, the elastic support beams 20 is also designed to establish a spring constant kz in the direction perpendicular to the receiving surface 11a of the magnetic disk 11 so as to accept the displacement of the contacting member 12 relative to the slider body 15 in the direction normal to the receiving surface 11a of the magnetic disk 11. In this manner, the contacting member 12 is allowed to move relative to the slider body 15.

An electrostatic actuator 22 as a driving power source is mounted on the slider body 15 for establishing a vertical driving force acting in the direction normal to the receiving surface 11a. The electrostatic actuator 22 is designed to include electrodes 23 formed on the insulating bottom layer 16, and conductive pads 24 formed on the contacting member 12 so as to oppose its surface to the electrodes 23, respectively. The electrostatic actuator 22 serves to generate the vertical driving force in response to the magnitude of voltage V applied to the air layer interposed between the electrodes 23 and the conductive pads 24. The contacting member 12 itself may be made of a conductive body in place of the formation of the conductive pads 24 over the contacting member 12.

Next, a detailed description will be made on a method of measuring the coefficient of friction according to a first embodiment of the present invention. The magnetic disk 11 is first driven to rotate at a higher rotational speed such as 7,000 rpm or 10,000 rpm, for example. Airflow is generated along the receiving surface 11a on the magnetic disk 11 and acts on the air bearing surface over the insulating bottom layer 16 in the head slider 13. The head slider 13 is allowed to fly above the receiving surface 11a at a predetermined flying height. The contacting member 12 is still kept distanced from the receiving surface 11a. Here, the rotational speed of the magnetic disk 11 is kept constant. Also, the flying height of the flying head slider 13 is kept constant in the following measurement of the coefficient of dynamic friction.

Figure 5A:
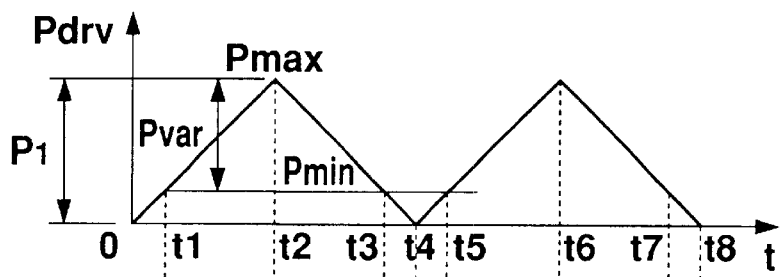
FIGS. 5A to 5D are timing charts for a method of measuring the coefficient of friction according to a first embodiment of the present invention.

The voltage V is then applied to the electrostatic actuator 22. The electrostatic actuator 22 generates a vertical driving force Pdrv acting on the contacting member 12. In this case, the vertical driving force Pdrv is linearly increased from "0(zero)." As shown in FIG. 5A, the vertical driving force Pdrv is repeatedly increased and decreased by the amplitude P1, for example. The vertical driving force Pdrv is allowed to take a triangle waveform.

Figure 5B:
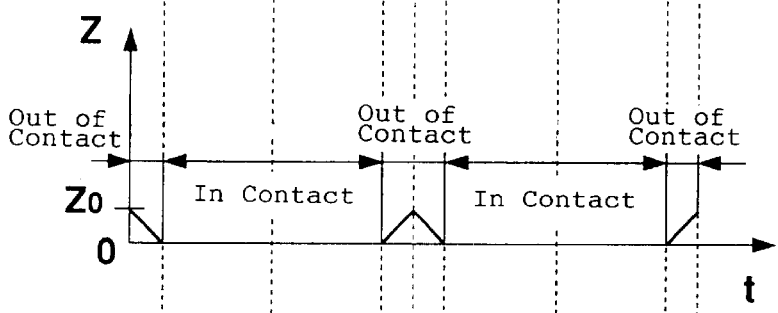

When the vertical driving force Pdrv is increased from zero, the contacting member 12 is driven to move toward the receiving surface 11a, as is apparent from FIG. 5B. No urging force Pload acts on the contacting member 12 at the moment when the contacting member 12 is finally allowed to contact or touch the receiving surface 11a. Accordingly, no friction is generated between the contacting member 12 and the receiving surface 11a in contact with the contacting member 12 at this moment. However, a lubricating agent or oil spreading over the receiving surface 11a generates adsorption acting on the contacting member 12 so as to generate an adsorptive tangential force transmitted from the receiving surface 11a to the contacting member 12. The adsorptive tangential force serves to drag the contacting member 12 with the assistance of the rotation of the magnetic disk 11 so as to generate the displacement of the contacting member 12 in the direction of rotation ROD. The vertical driving force Pdrv at this moment is hereinafter referred to as an initial contact vertical driving force Pmin.

Figure 5C:
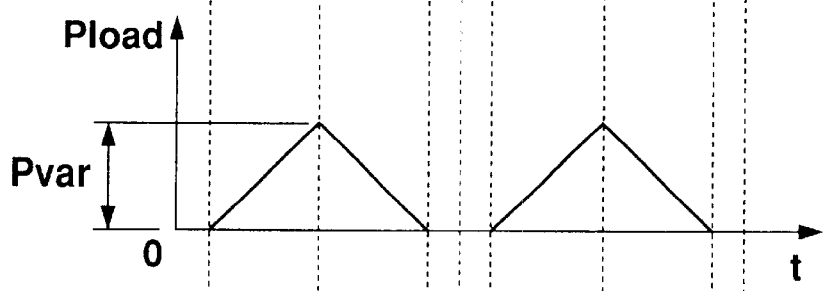

As the vertical driving force Pdrv is further increased, the urging force Pload starts to act on the contacting member 12 so as to urge the contacting member 12 against the receiving surface 11a. The urging force Pload is increased from zero in proportion to the increase in the vertical driving force Pdrv, as shown in FIG. 5C. The increase in the urging force Pload allows an increase in the friction established between the receiving surface 11a and the contacting member 12. The increased friction results in an increase in the overall tangential force transmitted from the receiving surface 11a to the contacting member 12. The increase in the overall tangential force induces an increase in the displacement of the contacting member 12 in the direction of rotation ROD.

When the vertical driving force Pdrv has reached the upper limit of the amplitude P1, namely, the maximum urging force Pmax, the maximum overall tangential force is transmitted from the receiving surface 11a to the contacting member 12. The overall tangential force is supposed to represent the sum of the adsorptive tangential force and the friction between the receiving surface 11a and the contacting member 12 based on the normal reaction established in response to the differential Pvar between the maximum urging force Pmax and the initial contact vertical driving force Pmin.

Thereafter, when the vertical driving force Pdrv starts to decrease, the urging force Pload acting on the contacting member 12 is also decreased. A still further decrease in the vertical driving force Pdrv serves to finally allow the contacting member 12 to get distanced from the receiving surface 11a. As long as the vertical driving force Pdrv is varied within the set amplitude P1 in the aforementioned manner, the contacting member 12 repeats the aforementioned action.

The coefficient of dynamic friction $\mu$ between the receiving surface 11a and the contacting member 12 is estimated based on the differential Pvar between the maximum urging force Pmax and the initial contact vertical driving force Pmin as well as the differential Dvar between the overall tangential force and the adsorptive tangential force. The divide of the differential Dvar by the differential Pvar leads to derivation of the accurate coefficient of dynamic friction $\mu$ eliminating the effect of the adsorption.

The overall tangential force and the adsorptive tangential force can be measured based on the spring constant ky of the elastic support beams 20 supporting the contacting member 12 and the displacement Y of the contacting member 12 in the direction of rotation ROD, namely, the direction along the receiving surface 11a. The product of the spring constant ky and the displacement Y represents the tangential force. The laser Doppler velocimeter 18 serves to derive the displacement Y of the contacting member 12. The laser Doppler velocimeter 18 is designed to detect the speed of movement of the contacting member 12. The integration of the measured speed reveals the displacement Y of the contacting member 12.

Figure 5D:
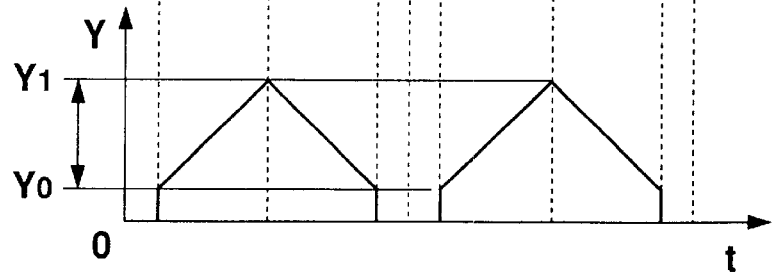

For example, if the increase and decrease of the vertical driving force Pdrv are repeated in the aforementioned manner, as shown in FIG. 5A, the measurement reveals the displacement Y as shown in FIG. 5D. A rapid rise or shift from zero to the level of Y0 can be observed in the displacement Y at the moment when the contacting member 12 has contacted or touched the receiving surface 11a. The level of Y0 is supposed to represent the displacement Y at the initial contact vertical driving force Pmin. The product of Y0 and the spring constant ky corresponds to the adsorptive tangential force at the initial contact vertical driving force Pmin. Since the displacement Y1 at the maximum urging force Pmax corresponds to the peak in the displacement Y, the overall tangential force at the maximum urging force Pmax can likewise be derived from the peak in the displacement Y. The product of the spring constant ky and the difference (Y1–Y0) reveals the differential Dvar corresponding to the differential Pvar.

The initial contact vertical driving force Pmin can be derived from the comparison between the variation in the vertical driving force Pdrv as shown in FIG. 5A and the variation in the overall tangential force. As described above, the variation in the overall tangential force is equivalent to the variation in the displacement Y as shown in FIG. 5D. As is apparent from the comparison between FIGS. 5A and 5D, the displacement Y behaves in a manner different from the vertical driving force Pdrv when the contacting member 12 is kept distanced from the receiving surface 11a. On the other hand, the displacement Y follows the behavior of the vertical driving force Pdrv when the contacting member 12 keeps contacting the receiving surface 11a. If the vertical driving force Pdrv can properly be determined at the moment when the displacement Y0 has occurred, the initial contact vertical driving force Pmin can be derived.

Otherwise, if the displacement Z0 of the contacting member 12 during movement toward the receiving surface 11a is properly determined, the initial contact vertical driving force Pmin can be derived, as is apparent from FIG. 5B. The product of the displacement Z0 and the spring constant kz is equivalent to the initial contact vertical driving force Pmin.

In addition, the adsorption Pa can also be calculated based on the multiplication of Y0 by ky. The adsorption Pa is supposed to depend on the contact area between the receiving surface 11a and the contacting member 12 of the head slider 13 in a magnetic disk drive. Individual derivation of the coefficient of dynamic friction $\mu$ and the adsorption Pa is supposed to contribute to a fine or still accurate analysis or observation for the action of the contacting member 12 or the head slider 13. The coefficient of dynamic friction $\mu$ is one of the most important factors when the abrasion and/or durability are considered for a head slider in a magnetic disk drive, while the adsorption Pa is one of the most important factors when the contact area is considered between a head slider and a magnetic disk in a magnetic disk drive.

Next, a detailed description will be made on a method of measuring the coefficient of friction according to a second embodiment of the present invention. The method of the second embodiment allows the contacting member 12 to keep contacting the receiving surface 11a, moving at the constant velocity, during measurement of the coefficient of dynamic friction $\mu$. The aforementioned measuring apparatus 10 may also be employed in this method of the second embodiment.

Figure 6A:
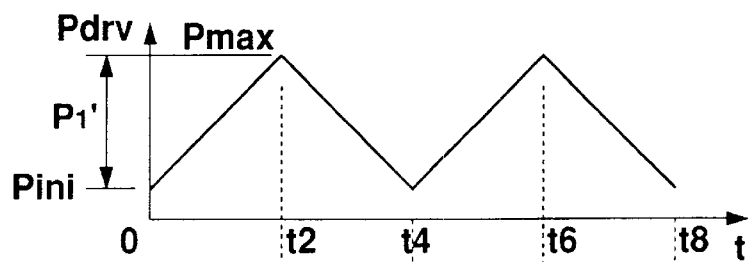
FIGS. 6A to 6C are timing charts for a method of measuring the coefficient of friction according to a second embodiment of the present invention.

As shown in FIG. 6A, the contacting member 12 is urged against the receiving surface 11a of the rotating magnetic disk 11 with a first vertical driving force Pini. The vertical driving force Pdrv is then linearly increased from the first vertical driving force Pini until the vertical driving force Pdrv reaches a second vertical driving force Pmax. The vertical driving force Pdrv is repeatedly increased and decreased by the amplitude P1', for example. The vertical driving force Pdrv is allowed to take a triangle waveform.

Figure 6B:
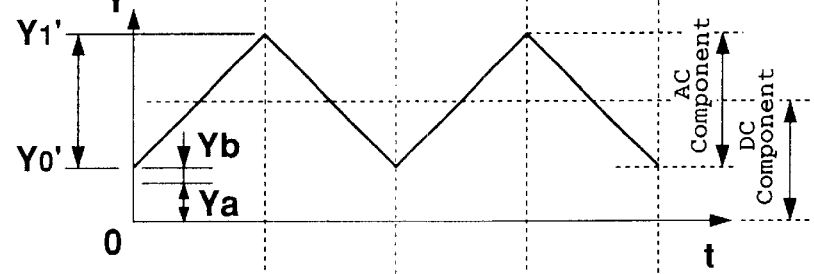
Figure 6C:
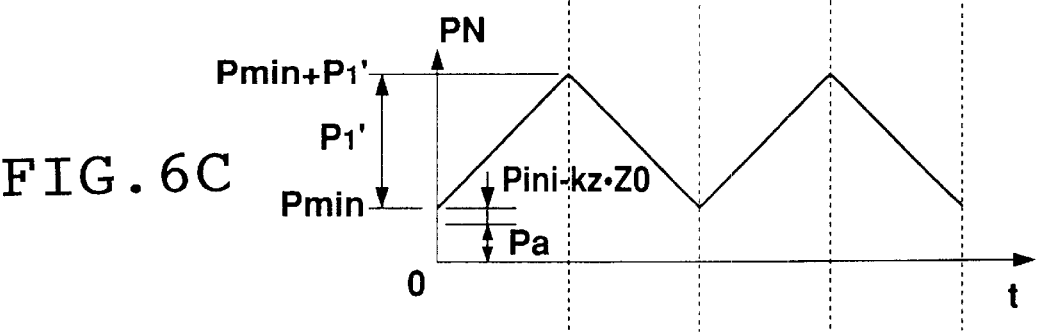

As shown in FIG. 6C, the normal reaction Pmin at the first vertical driving force Pini can be divided into a component under the influence of an adsorption Pa and a component under the influence of an urging force Pload. Here, the first vertical driving force Pini can be divided into the urging force Pload and a vertical driving force kz×Z0, equivalent to the spring force of the elastic support beams 20, required to move the contacting member 12 until the contacting member 12 contacts or touches the receiving surface 11a. Accordingly, when the vertical driving force kz×Z0 is subtracted from the first vertical driving force Pini, the urging force Pload can be obtained. The thus derived urging force Pload and the adsorption Pa are both supposed to be kept constant during variation in the vertical driving force Pdrv. The coefficient of dynamic friction $\mu$ between the receiving surface 11a and the contacting member 12 can be derived from the magnitude of the amplitude P1', namely, the differential between the first and second vertical driving forces Pini, Pmax, and the differential Dvar between the tangential forces transmitted from the receiving surface 11a to the contacting member 12 when the first and second vertical driving forces Pini, Pmax are respectively applied to. The divide of the differential Dvar by the amplitude P1' leads to derivation of the accurate coefficient of dynamic friction $\mu$ eliminating the effect of the adsorption.

The tangential forces can be measured based on the spring constant ky of the elastic support beams 20 supporting the contacting member 12 and the displacement Y of the contacting member 12 in the direction along the receiving surface 11a. The product of the spring constant ky and the displacement Y corresponds to the tangential force. The laser Doppler velocimeter 18 can be employed to determine the displacement Y in the aforementioned manner.

For example, if the increase and decrease of the vertical driving force Pdrv are repeated as shown in FIG. 6A, the measurement reveals the displacement Y as shown in FIG. 6B. The displacement Y0' at the first vertical driving force Pini is supposed to correspond to the minimum of the displacement Y, while the displacement Y1' at the second vertical driving force Pmax is likewise supposed to correspond to the maximum of the displacement Y. If the difference (Y1'-Y0') is multiplied by the spring constant ky, the differential Dvar corresponding to the amplitude P1' can be derived in a facilitated manner.

When the adsorption of the lubricating agent or oil is intended to be extracted from the overall tangential force transmitted from the receiving surface 11a to the contacting member 12, the overall tangential force at the first vertical driving force Pini may be divided into a component under the influence of the urging force Pload and a component under the influence of the adsorption Pa. Specifically, the displacement Y0' at the first vertical driving force Pini may be divided into a component Yb under the influence of the urging force Pload and a component Ya under the influence of the adsorption Pa.

First of all, the minimum urging force Pmin at the first vertical driving force Pini is calculated based on Pmin=Pini−kz×Z0 where kz represents the spring constant of the elastic support beams 20 and Z0 represents the displacement of the contacting member 12 during movement toward the receiving surface 11a. The component Yb of the displacement Y0' is then calculated based on Yb=$\mu$Pmin/ky utilizing the derived minimum urging force Pmin and the estimated coefficient of dynamic friction $\mu$. When the component Yb under the influence of the urging force Pload is subtracted from the displacement Y0', the component Ya, under the influence of the adsorption Pa, included in the displacement Y0' can be obtained. The adsorption Pa can thus be calculated based on Pa=Ya×ky/$\mu$.

The method of measuring according to the second embodiment enables derivation of the coefficient of dynamic friction $\mu$ and the adsorption Pa based on the waveform analysis. In this case, the output waveform of the displacement Y may be divided into an alternating current (AC) component and a direct current (DC) component, as shown in FIG. 6B, for example.

Figure 7:
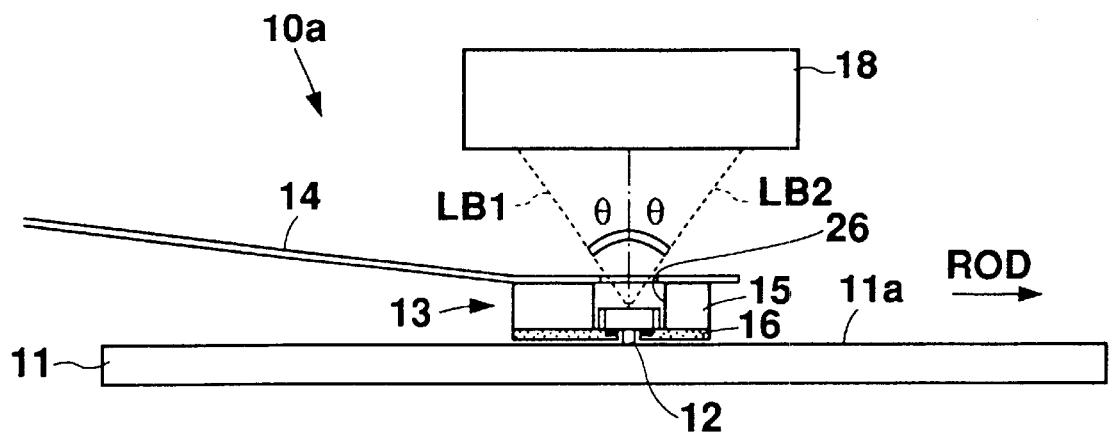
FIG. 7 is a side view, corresponding to FIG. 2, schematically illustrating a measuring apparatus including a laser Doppler velocimeter opposed to a receiving surface.

The measuring apparatus 10a may include the laser Doppler velocimeter 18 opposed to the receiving surface 11a behind the head slider 13 opposed to the receiving surface 11, as shown in FIG. 7, for example. A window opening 26 may be defined in the head suspension 14 and the slider body 15, respectively. The laser beams LB1, LB2 irradiated from the laser Doppler velocimeter 18 is introduced into the window opening 26 so as to reach the contacting member 12. In this measuring apparatus 10a, it is not necessary to employ a transparent material for the magnetic disk 11 defining the receiving surface 11a.

Figure 8:
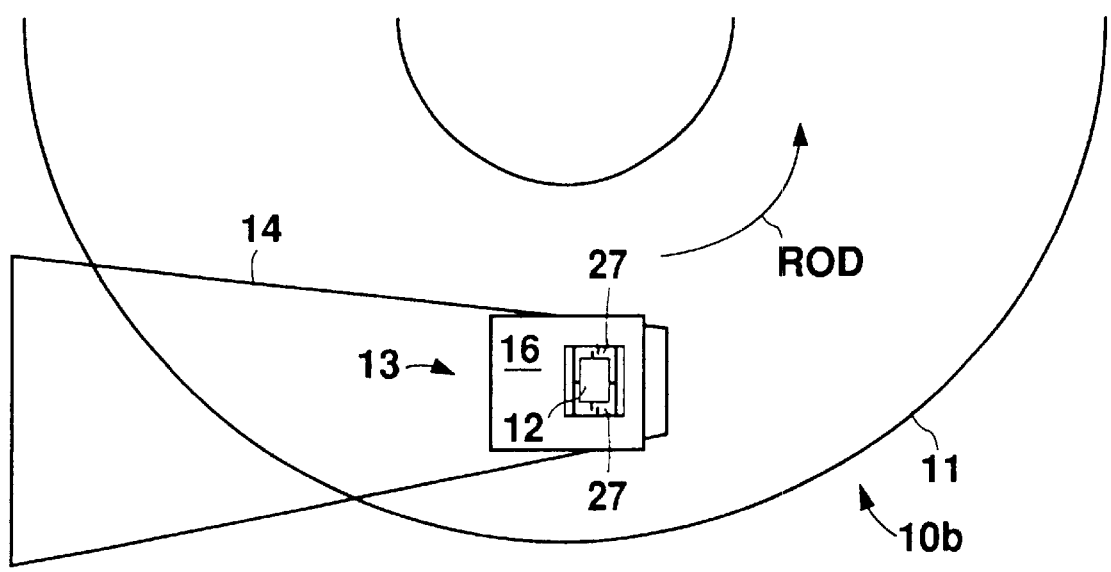
FIG. 8 is a plan view, corresponding to FIG. 1, illustrating a head slider including a capacitance displacement sensor.

Furthermore, the laser Doppler velocimeter 18 may be replaced with a capacitance displacement sensor 27 incorporated in the slider body 15 in the measuring apparatus 10b, as shown in FIG. 8, for example. The capacitance displacement sensor 27 is designed to detect the displacement Y of the contacting member 12. It is possible to measure the coefficient of dynamic friction $\mu$ and the adsorption Pa in a condition similar to the actual environment of a magnetic disk drive including the contacting member 12 on which electromagnetic transducers or read/write elements are mounted.

It should be noted that the coefficient of friction can be measured for any types of disk or recording medium rather than the aforementioned magnetic disk 11. Additionally, the aforementioned vertical driving force Pdrv in the first and second embodiments may represent any vertical component of any force acting on the contacting member 12 in the direction oblique to the normal direction to the receiving surface 11a.

What is claimed is:

1. A method of measuring a coefficient of friction, comprising:
   moving a receiving surface;
   applying to a slider a vertical driving force perpendicular to the receiving surface until the slider contacts the receiving surface;
   measuring an adsorptive tangential force transmitted from the receiving surface to the slider at a moment when the slider contacts the receiving surface; and
   measuring an overall tangential force transmitted from the receiving surface to the slider when the slider is urged against the receiving surface with an urging force.

2. The method of measuring according to claim 1, wherein steps of applying, measuring the adsorptive tangential force and measuring the overall tangential force are repeated.

3. The method of measuring according to claim 2, wherein said adsorptive and overall tangential forces are calculated based on a tangential spring constant of a support spring supporting the slider and a displacement of the slider in a direction along the receiving surface.

4. The method of measuring according to claim 3, wherein said displacement in the direction along the receiving surface is measured based on the Doppler effect of a laser irradiated on the slider.

5. The method of measuring according to claim 1, further comprising:
   continuously increasing the vertical driving force so as to generate the urging force;
   measuring a variation in the vertical driving force;
   measuring a variation in the tangential forces from the moment when the adsorptive tangential force has occurred until the overall tangential force reaches a maximum; and estimating an initial contact vertical driving force at a moment when the adsorptive tangential force starts to act on the slider, based on the variation in the vertical driving force and the variation in the tangential forces.

6. The method of measuring according to claim 5, wherein said initial contact vertical driving force is calculated based on a spring constant of a support spring supporting the slider and a displacement of the slider in a direction toward the receiving surface.

7. The method of measuring according to claim 6, said displacement in the direction toward the receiving surface is measured based on the Doppler effect of a laser irradiated on the slider.

8. The method of measuring according to claim 7, wherein said adsorptive and overall tangential forces are calculated based on a tangential spring constant of the support spring and a displacement of the slider in a direction along the receiving surface.

9. The method of measuring according to claim 8, wherein said displacement in the direction along the receiving surface is measured based on the Doppler effect of the laser irradiated on the slider.

10. The method of measuring according to claim 5, further comprising:

calculating a differential between the overall and adsorptive tangential forces;

calculating a differential between the initial contact vertical driving force and the urging force urging the slider against the receiving surface; and estimating the coefficient of friction based on the calculated differentials.

11. The method of measuring according to claim 10, wherein said adsorptive and overall tangential forces are calculated based on a tangential spring constant of a support spring supporting the slider and a displacement of the slider in a direction along the receiving surface.

12. The method of measuring according to claim 11, wherein said displacement in the direction along the receiving surface is measured based on the Doppler effect of a laser irradiated on the slider.

13. A method of measuring a coefficient of friction, comprising:

moving a receiving surface;

urging a slider against the receiving surface with a first load;

urging the slider against the receiving surface with a second load larger than the first load; and measuring a tangential force transmitted from the receiving surface to the slider when the first and second loads are respectively applied to the slider.

14. The method of measuring according to claim 13, wherein said second load is varied in a range including a value of the first load.

15. The method of measuring according to claim 14, wherein the coefficient of friction is estimated based on a predetermined differential between the first and second loads and a differential between the tangential forces for the respective first and second loads.

16. The method of measuring according to claim 15, wherein said tangential forces are calculated based on a tangential spring constant of a support spring supporting the slider and a displacement of the slider in a direction along the receiving surface.

17. The method of measuring according to claim 16, wherein said displacement in the direction along the receiving surface is measured based on the Doppler effect of a laser irradiated on the slider.

18. The method of measuring according to claim 16, wherein a capacitance displacement sensor is employed to detect the displacement in the direction along the receiving surface.

* * * * *